US008738151B2

(12) United States Patent
Nelson

(10) Patent No.: US 8,738,151 B2
(45) Date of Patent: May 27, 2014

(54) BODY PORTAL ANCHORS AND SYSTEMS

(75) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 220 days.

(21) Appl. No.: 13/090,482

(22) Filed: Apr. 20, 2011

(65) Prior Publication Data

US 2011/0270187 A1    Nov. 3, 2011

Related U.S. Application Data

(60) Provisional application No. 61/328,855, filed on Apr. 28, 2010.

(51) Int. Cl.
*A61N 1/00* (2006.01)

(52) U.S. Cl.
USPC ...... 607/116; 285/239; 604/164.01; 604/174; 604/175; 604/178; 604/288.02; 604/415; 604/48; 604/506; 604/510; 604/513; 604/533; 604/535; 604/65; 604/8; 606/129; 606/130; 607/115; 607/139

(58) Field of Classification Search
USPC .............. 128/207; 285/239; 604/164.01, 174, 604/175, 178, 288.02, 415, 48, 506, 510, 604/513, 533, 535, 65, 8; 606/129, 130; 607/115, 116, 139
See application file for complete search history.

(56) References Cited

U.S. PATENT DOCUMENTS

| | | | | | |
|---|---|---|---|---|---|
| 3,724,882 | A | * | 4/1973 | Dehar | 285/243 |
| 3,760,811 | A | | 9/1973 | Andrew | |
| 3,853,126 | A | * | 12/1974 | Schulte | 604/8 |
| 3,856,020 | A | * | 12/1974 | Kovac | 604/170.03 |
| 4,310,001 | A | * | 1/1982 | Comben | 607/37 |
| 4,328,813 | A | | 5/1982 | Ray | |
| 4,350,159 | A | | 9/1982 | Gouda | |
| 4,402,691 | A | * | 9/1983 | Rosenthal et al. | 604/411 |
| 4,473,369 | A | * | 9/1984 | Lueders et al. | 604/244 |
| 4,588,394 | A | * | 5/1986 | Schulte et al. | 604/9 |
| H150 | H | * | 11/1986 | Hankner et al. | 604/890.1 |
| 4,704,103 | A | * | 11/1987 | Stober et al. | 604/175 |
| 4,723,948 | A | * | 2/1988 | Clark et al. | 604/533 |
| 4,781,680 | A | * | 11/1988 | Redmond et al. | 604/288.02 |
| 4,880,414 | A | * | 11/1989 | Whipple | 604/533 |
| 4,929,236 | A | * | 5/1990 | Sampson | 604/175 |

(Continued)

FOREIGN PATENT DOCUMENTS

| | | |
|---|---|---|
| EP | 1 426 074 A1 | 6/2004 |
| EP | 1 426 074 B1 | 11/2006 |

(Continued)

OTHER PUBLICATIONS

U.S. Appl. No. 61/328,855, filed Apr. 28, 2010, Nelson.

*Primary Examiner* — Nicholas Lucchesi
*Assistant Examiner* — Scott Medway
(74) *Attorney, Agent, or Firm* — Mueting, Raasch & Gebhardt, P.A.

(57) ABSTRACT

Anchors for securing a therapy device such as a therapy catheter relative to a burr hole, and systems and methods for using the same. Anchors in accordance with embodiments of the present disclosure may include a connector for securing the therapy catheter to a delivery catheter, wherein the connector is independently and removably attachable to the anchor. The connector may secure the therapy catheter relative to the burr hole and isolate forces that may otherwise tend to disrupt the placement of the therapy catheter.

27 Claims, 10 Drawing Sheets

(56) References Cited

U.S. PATENT DOCUMENTS

| | | | |
|---|---|---|---|
| 4,995,856 A | 2/1991 | Heindl et al. | |
| 5,045,060 A * | 9/1991 | Melsky et al. | 604/288.02 |
| 5,129,891 A * | 7/1992 | Young | 604/533 |
| 5,178,612 A * | 1/1993 | Fenton, Jr. | 604/533 |
| 5,306,255 A * | 4/1994 | Haindl | 604/175 |
| 5,312,337 A * | 5/1994 | Flaherty et al. | 285/278 |
| 5,314,411 A * | 5/1994 | Bierman et al. | 604/174 |
| 5,464,446 A | 11/1995 | Dreessen et al. | |
| 5,527,307 A * | 6/1996 | Srisathapat et al. | 604/892.1 |
| 5,540,648 A * | 7/1996 | Yoon | 600/114 |
| 5,558,641 A * | 9/1996 | Glantz et al. | 604/288.02 |
| 5,685,858 A * | 11/1997 | Kawand | 604/171 |
| 5,702,371 A * | 12/1997 | Bierman | 604/180 |
| 5,713,858 A | 2/1998 | Heruth et al. | |
| 5,743,873 A * | 4/1998 | Cai et al. | 604/288.02 |
| 5,792,104 A * | 8/1998 | Speckman et al. | 604/288.02 |
| 5,795,335 A * | 8/1998 | Zinreich | 604/174 |
| 5,843,150 A | 12/1998 | Dreessen et al. | |
| 5,865,842 A | 2/1999 | Knuth et al. | |
| 5,913,852 A * | 6/1999 | Magram | 604/540 |
| 5,916,200 A | 6/1999 | Eppley et al. | |
| 5,927,277 A | 7/1999 | Baudino et al. | |
| 5,954,687 A | 9/1999 | Baudino | |
| 5,957,894 A * | 9/1999 | Kerwin et al. | 604/178 |
| 6,003,906 A * | 12/1999 | Fogarty et al. | 285/242 |
| 6,044,304 A | 3/2000 | Baudino | |
| 6,134,477 A | 10/2000 | Knuteson | |
| 6,213,973 B1 * | 4/2001 | Eliasen et al. | 604/93.01 |
| 6,290,677 B1 * | 9/2001 | Arai et al. | 604/183 |
| 6,321,104 B1 | 11/2001 | Gielen et al. | |
| 6,356,792 B1 | 3/2002 | Errico et al. | |
| 6,428,515 B1 * | 8/2002 | Bierman et al. | 604/174 |
| 6,478,783 B1 * | 11/2002 | Moorehead | 604/288.02 |
| 6,482,182 B1 | 11/2002 | Carroll et al. | |
| 6,572,587 B2 * | 6/2003 | Lerman et al. | 604/174 |
| 6,582,418 B1 * | 6/2003 | Verbeek et al. | 604/892.1 |
| 6,662,035 B2 * | 12/2003 | Sochor | 600/378 |
| 6,689,105 B2 * | 2/2004 | Tollini | 604/180 |
| 6,786,892 B2 * | 9/2004 | Bierman | 604/180 |
| 7,090,257 B2 * | 8/2006 | Werth | 285/243 |
| 7,107,104 B2 * | 9/2006 | Keravel et al. | 607/116 |
| 7,108,291 B2 * | 9/2006 | Baxi et al. | 285/257 |
| 7,204,840 B2 | 4/2007 | Skakoon et al. | |
| 7,331,613 B2 | 2/2008 | Schulte | |
| 7,374,557 B2 * | 5/2008 | Conlon et al. | 604/175 |
| 7,387,624 B2 * | 6/2008 | Nelson | 604/536 |
| 7,413,561 B2 * | 8/2008 | Raulerson et al. | 604/174 |
| 7,479,146 B2 * | 1/2009 | Malinowski | 606/130 |
| 7,540,857 B2 * | 6/2009 | Backman et al. | 604/180 |
| 7,553,298 B2 * | 6/2009 | Hunt et al. | 604/175 |
| 7,561,916 B2 * | 7/2009 | Hunt et al. | 607/36 |
| 7,580,756 B2 * | 8/2009 | Schulte et al. | 607/116 |
| 7,632,263 B2 * | 12/2009 | Denoth et al. | 604/523 |
| 7,766,394 B2 * | 8/2010 | Sage et al. | 285/321 |
| 7,811,266 B2 * | 10/2010 | Eliasen | 604/288.01 |
| 7,850,660 B2 * | 12/2010 | Uth et al. | 604/175 |
| 7,935,083 B2 * | 5/2011 | Bierman et al. | 604/174 |
| 7,981,119 B2 * | 7/2011 | Lando et al. | 606/129 |
| 8,007,474 B2 * | 8/2011 | Uth et al. | 604/175 |
| D650,475 S * | 12/2011 | Smith et al. | D24/108 |
| 8,075,531 B2 * | 12/2011 | Davey | 604/175 |
| 8,147,455 B2 * | 4/2012 | Butts et al. | 604/167.02 |
| 8,162,897 B2 * | 4/2012 | Byrum | 604/175 |
| 8,172,803 B2 * | 5/2012 | Morrissey et al. | 604/164.08 |
| 8,211,063 B2 * | 7/2012 | Bierman et al. | 604/174 |
| 8,262,630 B2 * | 9/2012 | Stats | 604/288.01 |
| 2002/0151871 A1 * | 10/2002 | Gaiser et al. | 604/510 |
| 2003/0199831 A1 | 10/2003 | Morris et al. | |
| 2005/0054985 A1 | 3/2005 | Mogg | |
| 2005/0143800 A1 | 6/2005 | Lando et al. | |
| 2005/0182425 A1 | 8/2005 | Schulte et al. | |
| 2005/0209573 A1 * | 9/2005 | Brugger et al. | 604/288.03 |
| 2005/0283119 A1 * | 12/2005 | Uth et al. | 604/175 |
| 2006/0095009 A1 * | 5/2006 | Lampropoulos et al. | 604/174 |
| 2006/0111688 A1 | 5/2006 | Kraus et al. | |
| 2006/0129126 A1 | 6/2006 | Kaplitt et al. | |
| 2006/0135945 A1 | 6/2006 | Bankiewicz et al. | |
| 2006/0149185 A1 * | 7/2006 | Gaiser et al. | 604/77 |
| 2006/0178647 A1 * | 8/2006 | Stats | 604/288.01 |
| 2006/0178648 A1 * | 8/2006 | Barron et al. | 604/288.02 |
| 2006/0247584 A1 * | 11/2006 | Sheetz et al. | 604/288.02 |
| 2006/0264898 A1 * | 11/2006 | Beasley et al. | 604/506 |
| 2007/0078391 A1 * | 4/2007 | Wortley et al. | 604/116 |
| 2007/0161958 A1 * | 7/2007 | Glenn | 604/175 |
| 2007/0270770 A1 * | 11/2007 | Bizup | 604/288.02 |
| 2008/0097287 A1 | 4/2008 | Nelson et al. | |
| 2008/0114308 A1 * | 5/2008 | di Palma et al. | 604/246 |
| 2008/0172068 A1 | 7/2008 | Adams et al. | |
| 2009/0093768 A1 * | 4/2009 | Conlon et al. | 604/175 |
| 2009/0143740 A1 * | 6/2009 | Bierman et al. | 604/177 |
| 2009/0143764 A1 | 6/2009 | Nelson | |
| 2009/0157157 A1 * | 6/2009 | Schorn et al. | 607/149 |
| 2009/0187149 A1 | 7/2009 | Nelson | |
| 2011/0270230 A1 | 11/2011 | Sage et al. | |
| 2011/0270231 A1 | 11/2011 | Nelson | |
| 2012/0083739 A1 | 4/2012 | Nelson | |
| 2012/0083742 A1 | 4/2012 | Nelson | |

FOREIGN PATENT DOCUMENTS

| | | |
|---|---|---|
| WO | WO 97/42870 A1 | 11/1997 |
| WO | WO 98/08554 A1 | 3/1998 |
| WO | WO 03/068304 A1 | 8/2003 |
| WO | WO 2004/026161 A2 | 4/2004 |
| WO | WO 2004/026161 A3 | 7/2004 |
| WO | WO 2004/105640 A2 | 12/2004 |
| WO | WO 2004/105640 A3 | 8/2005 |

\* cited by examiner

BODY PORTAL ANCHORS AND SYSTEMS

RELATED APPLICATION(S)

This application claims the benefit of U.S. Provisional App. No. 61/328,855, filed Apr. 28, 2010, the content of which is incorporated herein by reference.

TECHNICAL FIELD

Embodiments of the present invention relate generally to medical devices and, more particularly, to anchors for securing a therapy delivery device (e.g., a catheter) within, or otherwise relative to, a body portal such as a cranial burr hole, and to systems and methods incorporating and using the same.

BACKGROUND

Medical procedures involving access to the brain through a burr hole in the skull are used to treat a variety of medical conditions. For example, electrical stimulation of the brain to relieve chronic pain, or for the treatment of movement disorders, may necessitate access via a burr hole. Similarly, burr holes are typically formed to allow implantation of a therapy catheter, e.g., an intraparenchymal (IPA) or intracerebroventricular catheter, to treat various ailments.

Use of a catheter to deliver a therapeutic agent to the brain generally involves the insertion of the catheter into the brain and dispensing the agent at the desired location. During a typical implantation procedure, an incision may be made in the scalp to expose the patient's skull. After forming a burr hole through the skull, the catheter may be inserted into the brain. To accurately place the catheter and avoid unintended injury to the brain, surgeons typically use stereotactic apparatus/procedures. One exemplary stereotactic apparatus is described in U.S. Pat. No. 4,350,159 to Gouda (incorporated herein by reference in its entirety), which may be used to position, for example, an electrode.

As one can appreciate, once an inserted device such as a catheter is properly positioned, it is important that it be adequately immobilized to prevent movement of its distal, therapy delivering tip from its intended location. Even minimal movement of the device tip may reduce therapeutic efficacy of some therapies. Accordingly, reliable methods and apparatus for anchoring and securing the device relative to the burr hole are desirable.

In typical implantations, a free or connecting end of the device (e.g., an IPA therapy catheter) may extend outside of the burr hole and be anchored, relative to the burr hole, with an anchoring device. The free end of the therapy catheter may then be tunneled beneath the skin and connected away from the anchor to a secondary or delivery catheter (e.g., via a connector pin) that is, in turn, coupled to a therapeutic source containing the therapeutic agent. As a result, the agent may be delivered through the delivery catheter and the therapy catheter to the desired location within the patient.

During and after implantation, various forces may act on the delivery catheter. These forces may occur as a result of certain bodily movements (e.g., neck movements, forces transmitted through the scalp, etc.) or from tissue-induced movement (e.g., tissue swelling). These forces may cause the delivery catheter to flex and/or pull relative to the connector pin. Depending on how securely the connector pin is anchored, such forces may ultimately be transmitted to the therapy catheter. If sufficient, these forces may undesirably shift the therapy catheter, and thus its therapy delivery tip, away from the intended location.

SUMMARY

The present invention may overcome these and other issues by providing, in one embodiment, a body portal anchor system including: a base operable to secure to tissue surrounding a body portal; and a connector selectively attachable to the base. The connector, when attached to the base, is operable to fluidly connect with a terminal segment of a therapy catheter associated with the base. The system also includes a retaining member movable, relative to the base, between: a disengaged position, wherein the retaining member is spaced-apart from the connector so that the connector may move relative to the base; and an engaged position, wherein the retaining member engages the connector and attaches the connector to the base.

In another embodiment, an infusion system is provided including: a therapy catheter defining a lumen; and a burr hole anchor. The burr hole anchor includes an annular base defining a central opening and an outer peripheral edge. The base is operable to secure to bone surrounding a burr hole. The base further defines a catheter connection channel extending from the central opening outwardly through the peripheral edge. The anchor further includes a tubular connector selectively insertable into the channel, wherein the connector includes a therapy tip such that, when the connector is fully inserted into the channel, the therapy tip is received within the lumen of the therapy catheter. A retaining member is also provided and positionable within an opening formed in the base, wherein the opening intersects the channel. The retaining member is movable within the opening, while the connector is fully inserted into the channel, between: a disengaged position, wherein the retaining member is spaced-apart from the connector; and an engaged position, wherein the retaining member passes through the channel such that the retaining member contacts the connector and immobilizes the connector relative to the base.

In yet another embodiment, a method for connecting an intra-cranial therapy catheter implanted in tissue to a delivery catheter is provided. The method includes: attaching a base of a burr hole anchor to bone surrounding a burr hole; and positioning a terminal segment of the therapy catheter within a channel formed in the base. The method further includes: inserting a connector into the channel until a therapy tip of the connector is located within a lumen of the therapy catheter; and positioning a movable retaining member in an engaged position such that it contacts both the connector and the base to secure the connector relative to the base.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein.

Figure 1:
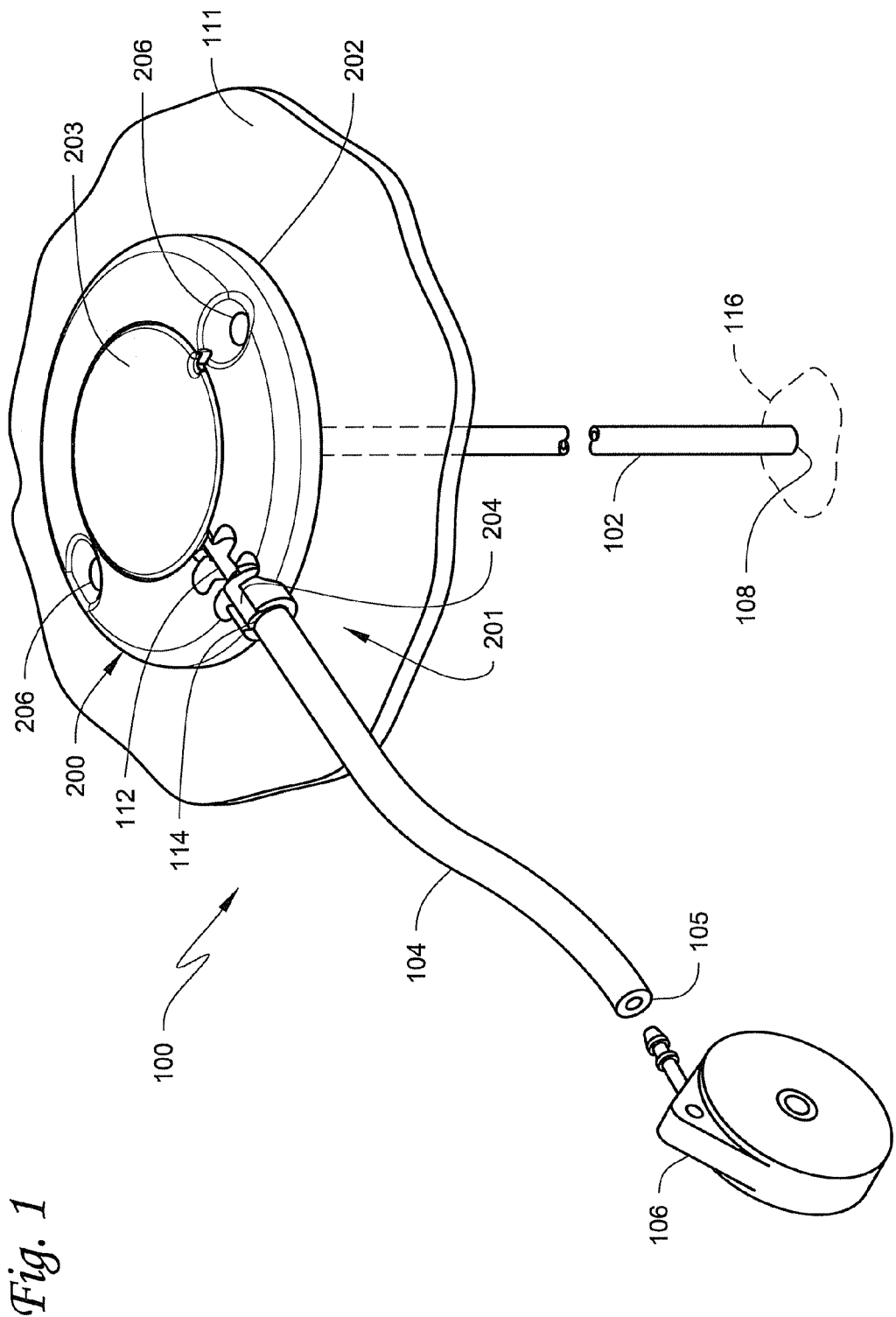
FIG. 1 is a diagrammatic perspective view of a therapy delivery system in accordance with one embodiment of the invention, the system including: a therapy source (e.g., an infusion pump); and an anchor system, an exemplary embodiment of which may include a body portal anchor (e.g., a burr hole anchor) and either or both of a delivery device (e.g., delivery catheter) and a therapy device (e.g., therapy catheter)

The figures are rendered primarily for clarity and, as a result, are not necessarily drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the instant invention may be directed to body portal anchor devices and assemblies and to corresponding body portal anchor systems and methods for securing a therapy device such as a therapy catheter relative to a body portal. For example, exemplary anchors described herein may be configured to secure a therapy device such as an IPA therapy catheter routed through a cranial burr hole. Such embodiments may further provide for connection of the therapy catheter with a delivery catheter that is fluidly connected to a therapy source.

Unlike some conventional anchor systems, anchors and systems in accordance with embodiments of the present invention may permit substantial isolation of the therapy catheter from forces that may act outside of the body portal, e.g., forces acting upon the delivery catheter. Moreover, systems, anchors, and methods in accordance with embodiments of the present invention may provide a catheter connector that may be selectively attached to the anchor during implantation (e.g., after the therapy catheter has been located). Such a construction may substantially reduce or prevent movement of the therapy catheter tip during subsequent connection of the therapy catheter with the delivery catheter. Various aspects of exemplary anchor devices, systems, and methods are further described below.

While described herein in the context of burr hole anchors and corresponding infusion systems, anchors and systems in accordance with embodiments of the present invention may find use in other medical (and non-medical) applications that involve access through a portal. Moreover, while described herein with reference to a brain infusion therapy catheter, embodiments of the invention may find application to other catheters and to other fluid conveying devices, as well as to other therapy devices, e.g., stimulation leads.

It is noted that the terms "comprises" and variations thereof do not have a limiting meaning where these terms appear in the accompanying description. Moreover, "a," "an," "the," "at least one," and "one or more" are used interchangeably herein. Further, relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

FIG. 1 illustrates an exemplary implantable medical system, such as a brain infusion system 100 as it may be configured during use, e.g., implantation. FIG. 1 is intended to be a diagrammatic representation of an exemplary system. As a result, the illustration may not represent an actual scaled snapshot of the system during or after implantation. Embodiments of the components described herein may be sized for use with burr holes typical in human and other mammalian applications. For example, in one embodiment, a central opening 208 (see, e.g., FIG. 2) may be about 14 millimeters (mm) in diameter. However, such a configuration is not limiting as exemplary anchors could be scaled to accommodate most any application without departing from the scope of the invention.

The exemplary infusion system 100 may include an anchor system 201 with a first medical tube, e.g., an intra-cranial IPA therapy catheter 102, which may be partially implanted within a mammalian brain 116. To assist with placement of the therapy catheter 102, a stereotactic apparatus as is known in the art may be utilized. In the illustrated example, the therapy catheter 102 is implanted through a body portal, e.g., through a burr hole 110 (the burr hole is located underneath a burr hole anchor 200 in FIG. 1; see FIGS. 2 and 7). The burr hole 110 may be formed in tissue (e.g., the bone forming the skull 111, which is represented diagrammatically in the figures), which is shown partially cut-away in FIG. 1 for clarity. Ultimately, once the catheter 102 is accurately implanted through the burr hole in the skull, a second end or tip 108 of the catheter is positioned at a predetermined location within the brain 116.

The infusion system (e.g., the anchor system 201) may further include a second medical tube, e.g., a feed or delivery catheter 104. The delivery catheter may have a second end 105 coupled to a therapy source or reservoir (e.g., an implantable infusion pump 106 such as a SynchroMed® II programmable infusion pump distributed by Medtronic, Inc., of Minneapolis, Minn. USA) containing a volume of the therapeutic agent. While described herein in the context of an implantable infusion pump 106, this configuration is not limiting. For example, other embodiments may replace the pump with most any internal or external medicament delivery device, e.g., syringe, drip bag, etc.

A first end 112 of the therapy catheter 102 may be routable through a cranial burr hole anchor device or assembly (referred to herein as "anchor 200"). In the illustrated embodiment, the first end 112 of the therapy catheter 102 may, via the anchor 200, be operatively connected to a corresponding first end 114 of the delivery catheter 104 (e.g., via a connector 204, exemplary embodiments of which may form a tubular member as described below).

The infusion system 100 may, in one embodiment, be configured to deliver a therapeutic agent for the treatment of a chronic ailment, e.g., convection-enhanced delivery (CED) of a medicament for the treatment of Huntington's disease. The therapeutic agent is delivered, via the catheters 102 and 104, from the pump 106 to the brain 116. This application is not limiting, however, as the system may be configured to deliver other therapeutic agents (e.g., such as for the treatment of Parkinson's or Alzheimer's disease) to the brain or to most any other region of the body.

With this general overview, the following description will address various exemplary embodiments and aspects of the anchor 200 and system 201, as well as methods for using the same. While these embodiments may be described with some degree of particularity, they are nonetheless intended to be exemplary. That is, those of skill in the art will recognize that other embodiments are certainly possible.

Figure 2:
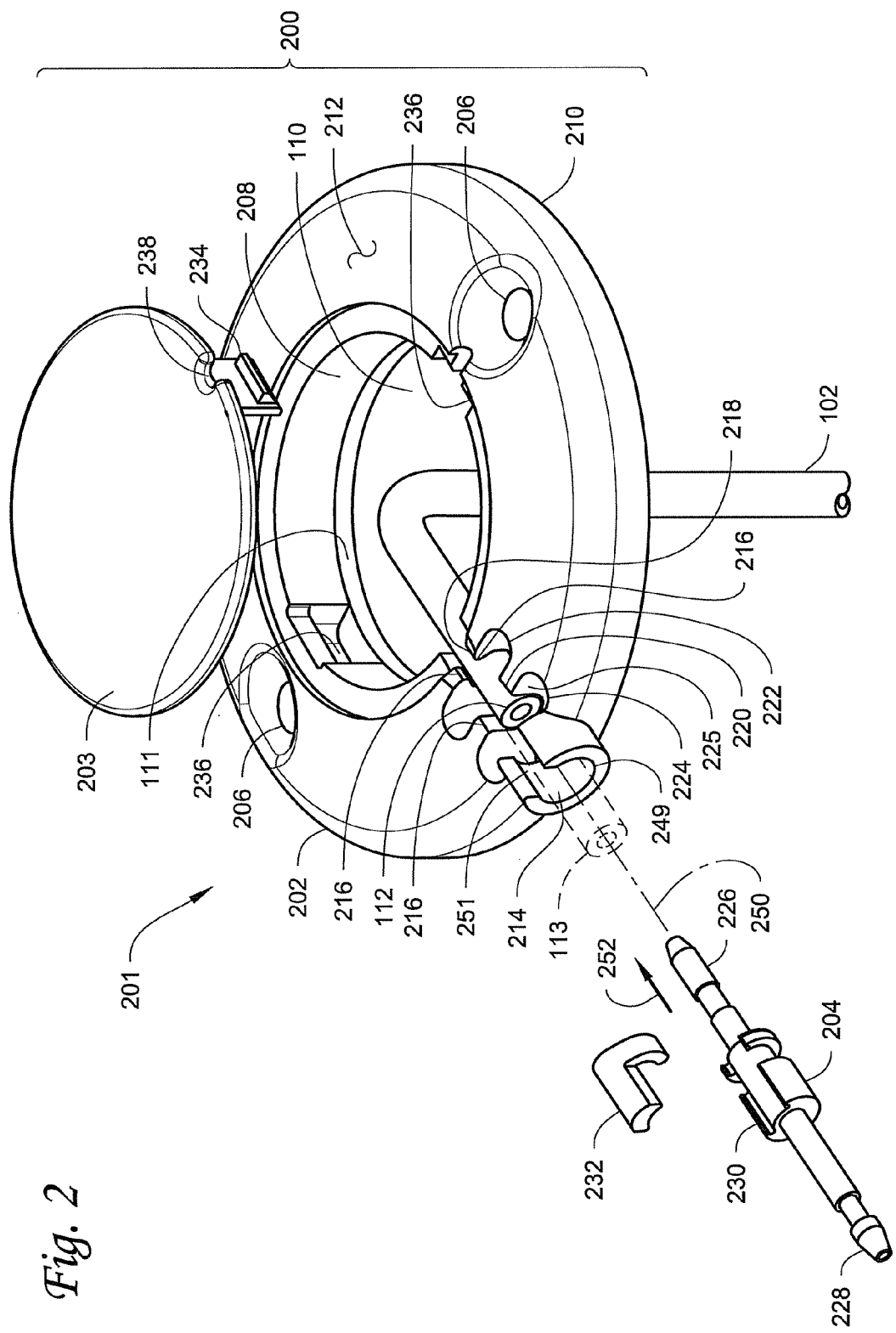
FIG. 2 is a partially exploded perspective view of the anchor of FIG. 1.

FIG. 2 illustrates an enlarged perspective view of the anchor system 201. As shown in this view, the anchor 200 may include an annular base 202 that may be positioned to surround the burr hole 110, and an optional cap 203. The anchor 200 (e.g., the base 202) may be operable to secure to the tissue, e.g., to an outer surface of the skull (bone 111) surrounding the burr hole 110 via any acceptable method. In the illustrated embodiment, the base 202 is secured with bone screws (not shown) extending through openings (e.g., holes 206) formed through the base 202. The system 201 may further include the tubular pin or connector 204 selectively attachable to the base as further described below.

The base 202 may define a central opening 208 that aligns coaxially with the burr hole 110 when the base is attached to the bone 111. The annular base 202 may further define an outer peripheral edge 210 and an upper surface 212. In the illustrated embodiments, the base, e.g., the face 212, may have a cutout or series of cutouts that define a catheter connection passage, e.g., a shaped catheter connection channel 214 extending from the central opening 208 outwardly to and through the peripheral edge 210. The channel 214 may, in the illustrated embodiments, be formed in the upper surface 212 of the base. As described in more detail below, the channel 214 may receive therein the first or terminal end 112 of the therapy catheter 102. A terminal segment of the catheter 102 (the end segment of the catheter that includes the first end 112) may be received and mechanically captured in the channel 214 by, in one embodiment, cinching surfaces 216 formed or defined by the channel. In the illustrated embodiments, cinching surfaces 216 are included at two discrete locations (cinching points 218 and 220). These surfaces may overhang portions of the channel as illustrated in the figures.

The channel 214 may be configured in most any acceptable manner that provides a passageway extending from the central opening 208 through the peripheral edge 210. However, in the illustrated embodiment, the channel 214 is configured as a relatively open-faced trough as shown in FIG. 2. As visible in this view, the channel 214 may be further defined by first and second enlarged areas 222 and 224. The purpose of the enlarged areas 222 and 224 is explained in more detail below.

In addition to receiving the catheter 102, the trough-like channel 214 may also receive therein the connector 204. As illustrated in the figures, the connector 204 may include a first end 226 defining a therapy tip for selective insertion into the channel 214, and an opposite or second end 228 defining a delivery tip. The connector 204 may further include an enlarged central portion 230 between the first and second ends. The first and second ends 226, 228 (e.g., the therapy tip and the delivery tip) may be configured for insertion into lumens of, respectively, the therapy catheter 102 and the delivery catheter 104. The shape and size of the first and second ends of the connector 204, as well as the size and material of the catheters, may be selected to produce a relatively secure and leak-free connection between the catheters and the connector when joined.

The system 201 may further include a retaining element or member, which in one embodiment, is configured as a detachable clip 232. The retaining member may be configured to engage the connector 204 and immobilize it relative to the base 202 after the connector is inserted into the channel 214 and the therapy catheter 102. While shown as a separate component in FIGS. 1-7, the retaining member could, in other embodiments, be integral to, or retained by, the connector (e.g., threads or pins) or, alternatively, integral with or retained by the anchor base 202. In fact, the retaining member may be of most any configuration that allows selective, clinician-initiated fixing of the connector relative to the base.

As used herein, the term "immobilize" and its variations refers to securing a first member to one or more second members such that little or no relative movement occurs between the first and second members. Those of skill in the art will realize that, for a variety of reasons (e.g., tolerances of parts), some minor relative movement may still occur between the members, but such movement is minimized and of little or no consequence to the intended operation of the immobilized member.

The cap 203 may include one or more elements, e.g., tabs 234, which interact with receiving elements, e.g., slots 236, formed in the base to permit snap-fit engagement of the cap to the base. The cap 203 may further include a slot or opening 238 to permit removal of the cap, e.g. via a prying action, from the base if desired.

While most any biocompatible material is suitable, the base 202 and cap 203 may, in one embodiment, be made from a hard plastic (e.g., polysulfone or polyetheretherketone (PEEK)) or metal such as grade 2 or grade 5 Titanium. The connector 204 and retaining clip may be made of the same or similar materials.

The catheter 102 may, in one embodiment, be similar or identical to the catheters described in U.S. Pat. App. Pub. 2009/0143764 A1 to Nelson and entitled INFUSION CATHETER ASSEMBLY WITH REDUCED BACKFLOW (incorporated herein by reference in its entirety). In other embodiments, the catheter 102 (as well as the catheter 104) may be of conventional construction and made from most any shearable material including, e.g., urethane, silicone, or blends of the same.

Figure 3:
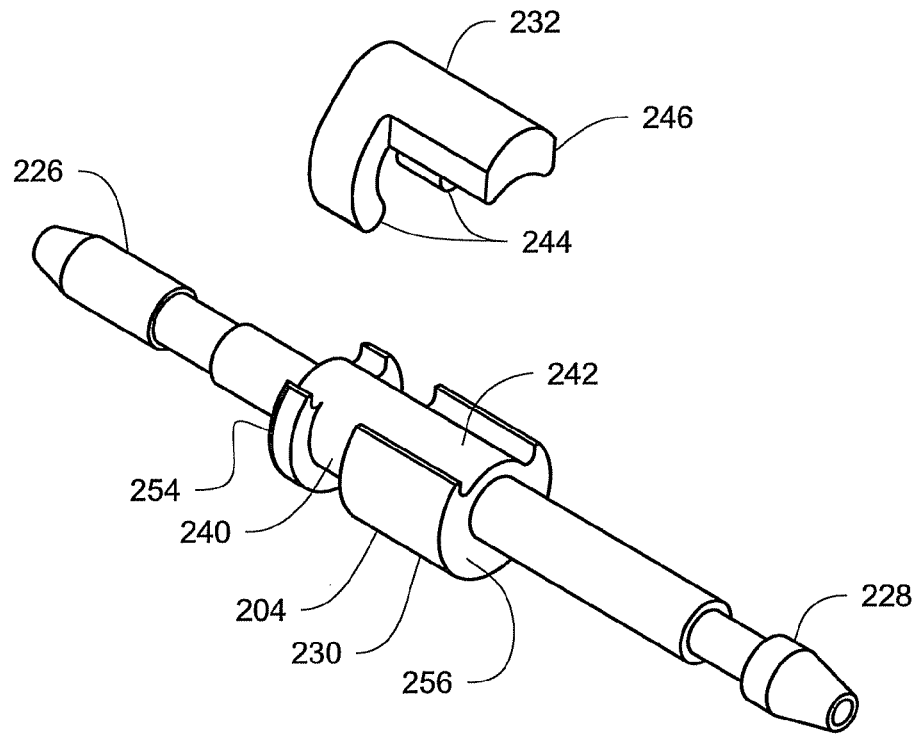
FIG. 3 is an enlarged perspective view of a connector and retaining member of the anchor of FIG. 2.

FIG. 3 illustrates an enlarged perspective view of the connector 204 and the clip 232 with the latter in a disengaged or detached position. As shown in this view, the enlarged central portion 230 of the connector 204 may include cutouts to receive the clip. For instance, an outer surface of the central portion 230 may include a circumferential groove 240 and an intersecting longitudinal groove 242. The circumferential groove 240 may be sized to partially receive therein two opposing resilient legs 244 of the clip, e.g., in a snap-fit relation. In the illustrated embodiment, the legs 244 are semi-cylindrical in shape to correspond with the shape of the groove 240. In a similar manner, the groove 242 may receive a body portion 246 of the clip. The body portion 246 may form a key or other anti-rotate feature configured to limit rotational movement of the connector and clip relative to the base when the connector is fully inserted into the channel 214 and the clip is placed in the engaged or attached position (see, e.g., FIG. 4). In the illustrated embodiment, this anti-rotate feature is achieved by providing corresponding keyway surfaces in the channel 214. The body portion 246 may also prevent rotation of the clip 232 relative to the connector 204 by fitting into the groove 242 of the connector.

Figure 4:
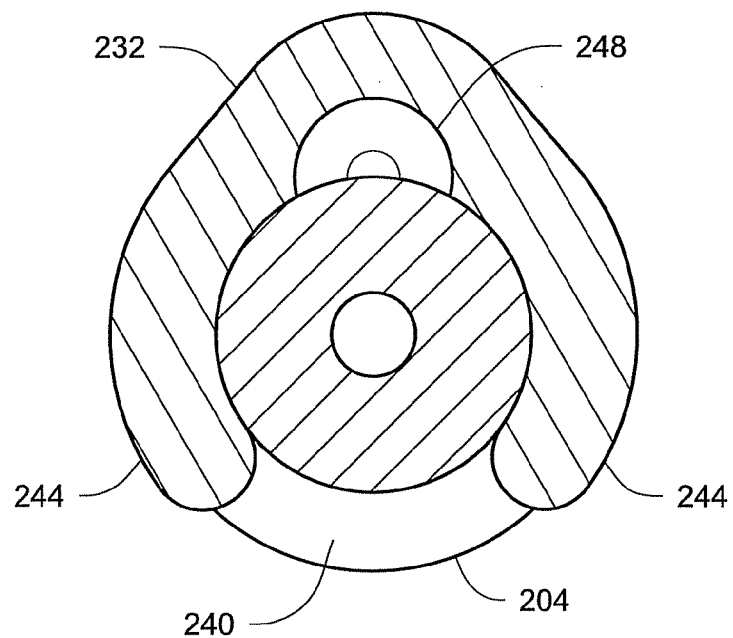
FIG. 4 is a cross sectional view of the connector and retaining member of FIG. 3 as assembled and viewed along a longitudinal axis of the connector.

FIG. 4 is a section view of the connector 204 and clip 232 taken normal to a longitudinal axis 250 (see FIG. 2) of the connector/channel and through the groove 240 when the clip is attached to the connector. FIG. 4 further illustrates a cutout 248 that may be formed in the clip, as well as the delivery lumen of the connector (which extends entirely through the connector). The cutout may accommodate a tool to pry the clip 232 and separate it from the connector when removal of the connector from the base 202 is desired. The clip 232 and/or connector 204 could also include features that permit attachment, e.g., tethering, to the anchor base 202 as a means of preventing the clip from being lost during attachment and detachment.

Use of the exemplary anchor system 201 will now be described with reference primarily to FIGS. 2 and 5-7. The intra-cranial therapy catheter 102 may be correctly positioned through the burr hole 110 (already formed) such that the implanted therapy delivering tip 108 (see FIG. 1) is located at the desired location within the brain 116. As stated above, stereotactic equipment and methods as are known in the art may be utilized to locate the catheter 102. The base 202 may typically be attached to the skull bone before catheter implantation. The therapy catheter may then be routed through the central opening 208 of the base 202 using the stereotactic apparatus, often with the aid of guide cannula and/or stylet. The base could also be attached after catheter 102 implantation. In this instance, the catheter 102 could be detached from the stereotactic apparatus and the anchor base 202 placed over the cut catheter (i.e., the exposed end of the catheter may be passed through the central opening) and attached to the skull. In alternate embodiments, the anchor base 202 could be slotted (e.g., C-shaped) to allow side-loading attachment during, before, or after placement (e.g., stereotactic placement) of the catheter 102.

Figure 5:
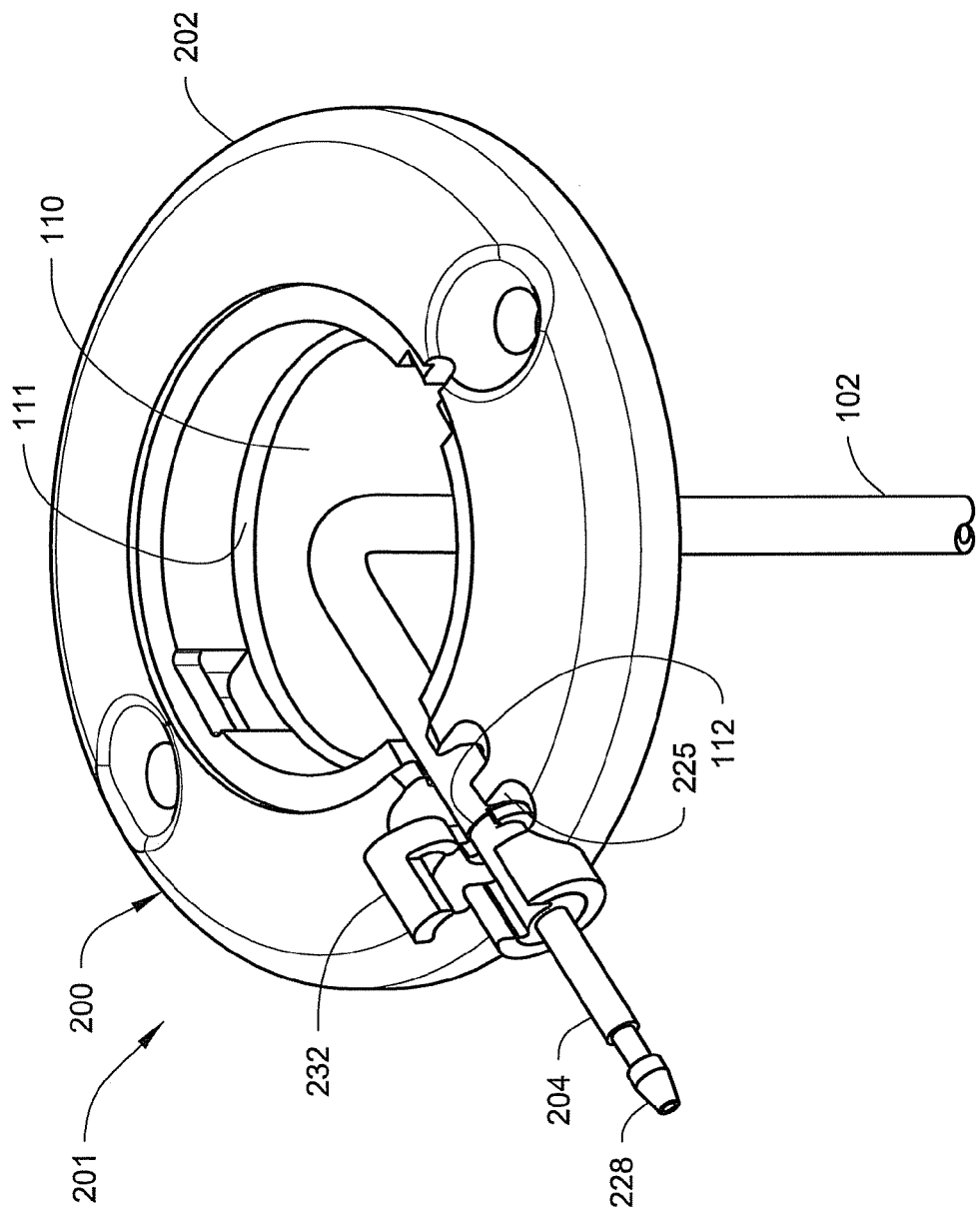
FIG. 5 is perspective view of the anchor of FIG. 2 with a connector shown in an attached or fully inserted position and the retaining member shown in a disengaged position.

The catheter may then be bent to pass through and lie within the channel 214 as shown in FIG. 2. With the trough-like channel 214 of the illustrated embodiment, the terminal segment of the therapy catheter may be pressed into the channel from above, e.g., the catheter 102 may enter the channel in a direction transverse or normal to the longitudinal axis 250 of the channel. As the catheter 102 is pressed into the channel, it may ultimately squeeze past the opposing cinching surfaces 216 at both the first and second cinching points 218 and 220. The cinching surfaces 216, as illustrated herein, are configured as an overhang over the channel 214 as best shown in FIGS. 2 and 5. This overhang may provide a narrow entry for the catheter into the channel 214. However, beyond the overhang, the channel may be of sufficient width to accommodate the catheter with a clearance fit.

While described herein as overhanging, the cinching surfaces 216 may be of most any design that permits mechanical capture of the catheter once the catheter is fully inserted into the channel, e.g., any design that limits movement of the catheter in at least the transverse direction (in a direction other than along the longitudinal axis 250 of the connector) back out of the channel. Regardless of the configuration, the channel 214 may effectively receive and contain the terminal segment of the therapy catheter 102 within the channel at one or more discrete locations (e.g., in the illustrated embodiment, at the two cinching points 218 and 220).

While described herein as utilizing mechanical capture elements or cinching surfaces, these aspects of the invention are optional. That is, alternative embodiments may do away with the overhanging cinching surfaces altogether. In such a configuration, a compliant catheter may simply be bent wherein it lies within a generally open channel. In this case, the catheter 102 could be held in place by a surgical instrument during the catheter connection process.

An unneeded, excess length or portion 113 of the catheter may now protrude outwardly from the outermost cinching point 220 as shown in the broken line representation in FIG. 2. To remove this excess portion 113 from the terminal segment of the catheter 102, the clinician may insert forceps or the like (not shown) into the first enlarged area 222 of the channel 214 to hold the catheter 102 while surgical scissors or a scalpel (not shown) are used to sever the excess portion 113. In the illustrated embodiment, the second enlarged cutout 224 is defined in part by a cut surface 225 (the cut surface may be adjacent one or more of the cinching surfaces in the illustrated embodiment) that may be used as a guide to trim the catheter 102. That is, the catheter 102 may be cut in the second enlarged area along the cut surface 225. After trimming and removing the excess portion 113 that extends beyond the cut surface 225, the resulting first end 112 of the catheter may be located within the channel 214 at or near the cut surface as shown in FIG. 2.

With the therapy catheter 102 now cut to length and positioned in the channel 214, the lumen of the therapy catheter is aligned with the channel and thus aligned with the first end of the connector 204. Accordingly, as the connector 204 is inserted into the channel 214, the therapy tip of the first end 226 of the connector may enter the lumen of the catheter 102, at which point the connector may be fluidly connected with the terminal segment of the catheter. In one embodiment, the connector 204 may be selectively inserted through a feed connector port 249 of the base 202 and along the longitudinal axis 250 as indicated by the arrow 252 in FIG. 2. In this embodiment, the channel 214 may be configured to limit movement of the connector 204 along generally all but the direction 252 (i.e., the channel may allow movement of the connector generally only along the longitudinal axis 250). Moreover, the feed connector port 249 may also be configured to restrict insertion of the connector to only the longitudinal direction, e.g., it may have a configuration that does not allow the connector to pass into the channel from above. While inserting the connector 204 into the channel 214, the catheter 102 may again be gripped with forceps or the like positioned within the first enlarged area 222. As illustrated in the figures, the first (and second) end of the connector 204 may have a shape conducive to insertion into the catheters, e.g., be conically shaped, radiused, or beveled to permit the ends of the connector to more easily enter the respective catheters.

Continued insertion of the connector 204 into the channel 214 may eventually result in contact between an annular face 254 (see FIG. 3) of the connector and the cut surface 225 of the base 202. This contact may limit further insertion of the connector into the channel as shown in FIG. 5. When the connector is fully inserted into the channel as shown in FIG.

5, the annular face 254 of the connector 204 may abut not only the cut surface 225, but also abut, or nearly abut, the first end 112 of the therapy catheter 102.

Once the connector 204 is fully inserted into the channel 214 and the catheter 102, the retaining member, e.g., clip 232, may be moved from the disengaged position (see, e.g., FIGS. 2, 3 and 5) to an engaged position (see, e.g., FIGS. 4 and 6) to secure the connector relative to the base 202. When in the disengaged position, the retaining member 232 may be spaced-apart from the connector 204 to allow movement of the connector relative to the base, e.g., within the channel or passage. However, when in the engaged position, the retaining member 232 engages the connector 204 and immobilizes it relative to the base 202.

Figure 6:
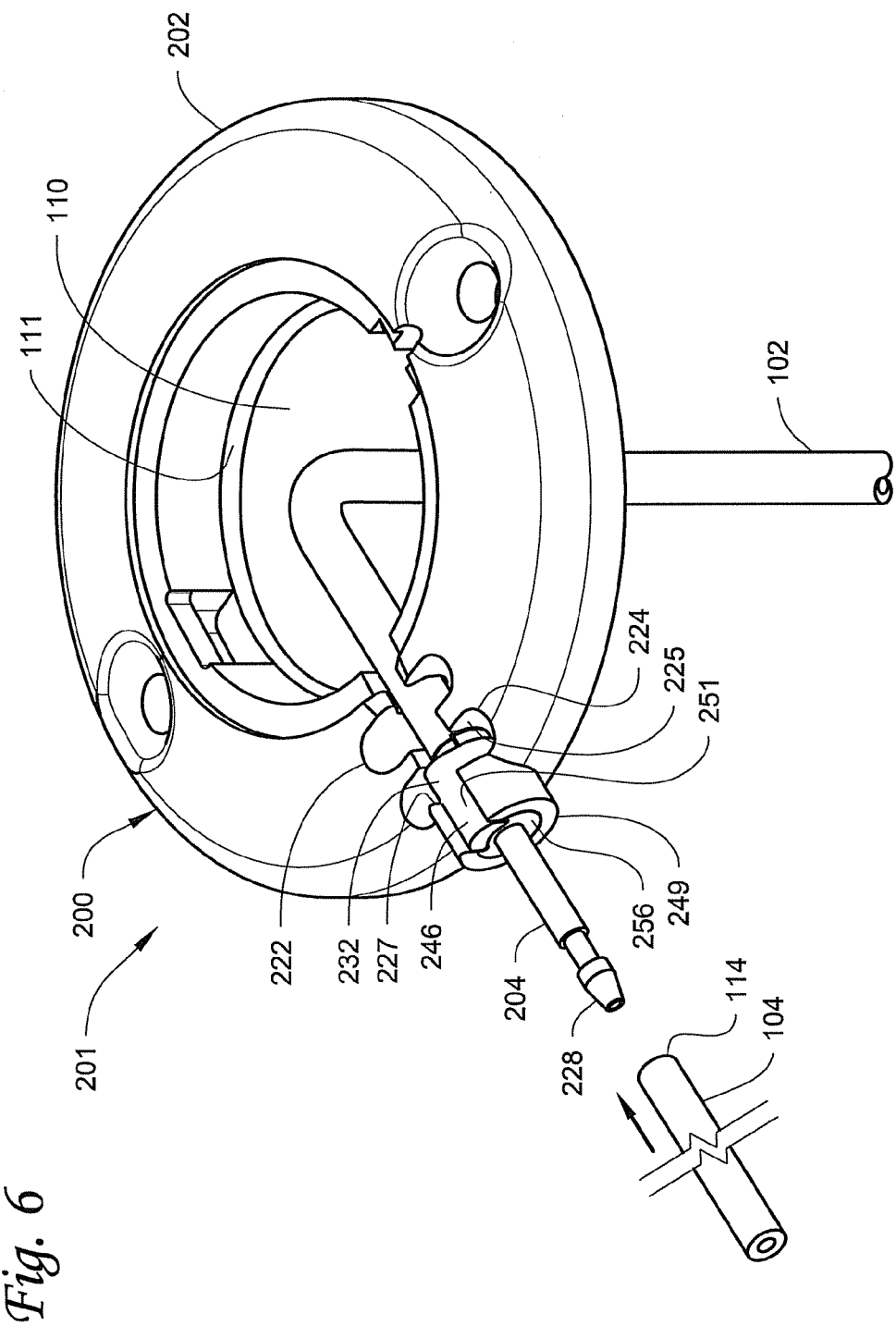
FIG. 6 is perspective view of the anchor of FIG. 5 with the retaining member shown in an engaged position with the connector.

To attach the clip 232 to the anchor, the clip (e.g., while held by forceps or the like) may be pressed onto the connector with sufficient force that the resilient legs 244 (see FIGS. 3 and 4) expand and then retract around the round portion of the connector within the circumferential groove 240. As evident in the figures, the clip 232 may engage the connector 204 (e.g., move from its disengaged to engaged positions) along a direction transverse or normal to the longitudinal axis 250. Once fully inserted into the groove 240, the clip 232 mechanically captures the connector 204 relative to the base 202, i.e., once the clip 232 is attached to the connector 204, the connector is effectively attached or fixed to the base. In the illustrated embodiment, the portions of the clip 232 that protrude beyond the outer diameter of the connector 204 may be accommodated by the second enlarged area 224. As also shown in FIG. 6, the clip 232 and annular face 254 of the connector 204 (see FIG. 3) may be restrained within the second enlarged opening 224, e.g., restrained between the cut surface 225 and a stop surface 227 defined by the second enlarged opening. As a result, axial movement of the connector 204 is substantially limited.

Similarly, the body portion 246 of the clip 232 (see FIGS. 3 and 6) may seat within a narrow slot 251 (see also FIG. 2) formed in the top of the feed connector port 249, as well as within the longitudinal groove 242 of the connector 204. By nesting within the slot 251, the body portion 246 may limit rotational movement of the connector relative to the base 202.

With the connector secured in the channel 214, the cap 203 (see FIG. 2) may be attached to the base 202 to cover the central opening 208 as described elsewhere herein. The first end 114 of the delivery catheter 104 (see FIGS. 1 and 6) may then be attached to the delivery tip (the second end 228) of the connector 204 by inserting the second end 228 into the catheter 104 until the catheter abuts a second annular face 256 of the connector (see FIGS. 3 and 6). The delivery catheter 104 may be coupled, as illustrated in FIG. 1, at its second end 105 to the pump 106 or other therapeutic source. In other embodiments, the delivery catheter 104 (see FIG. 1) could be attached to the connector 204 before the connector is attached to the base 202.

As stated elsewhere herein, due to the mechanical capture of the connector 204 to the base 202, the transmission of extraneous loads to the therapy catheter 102 from the delivery catheter 104 may be substantially reduced or eliminated.

Figure 7:
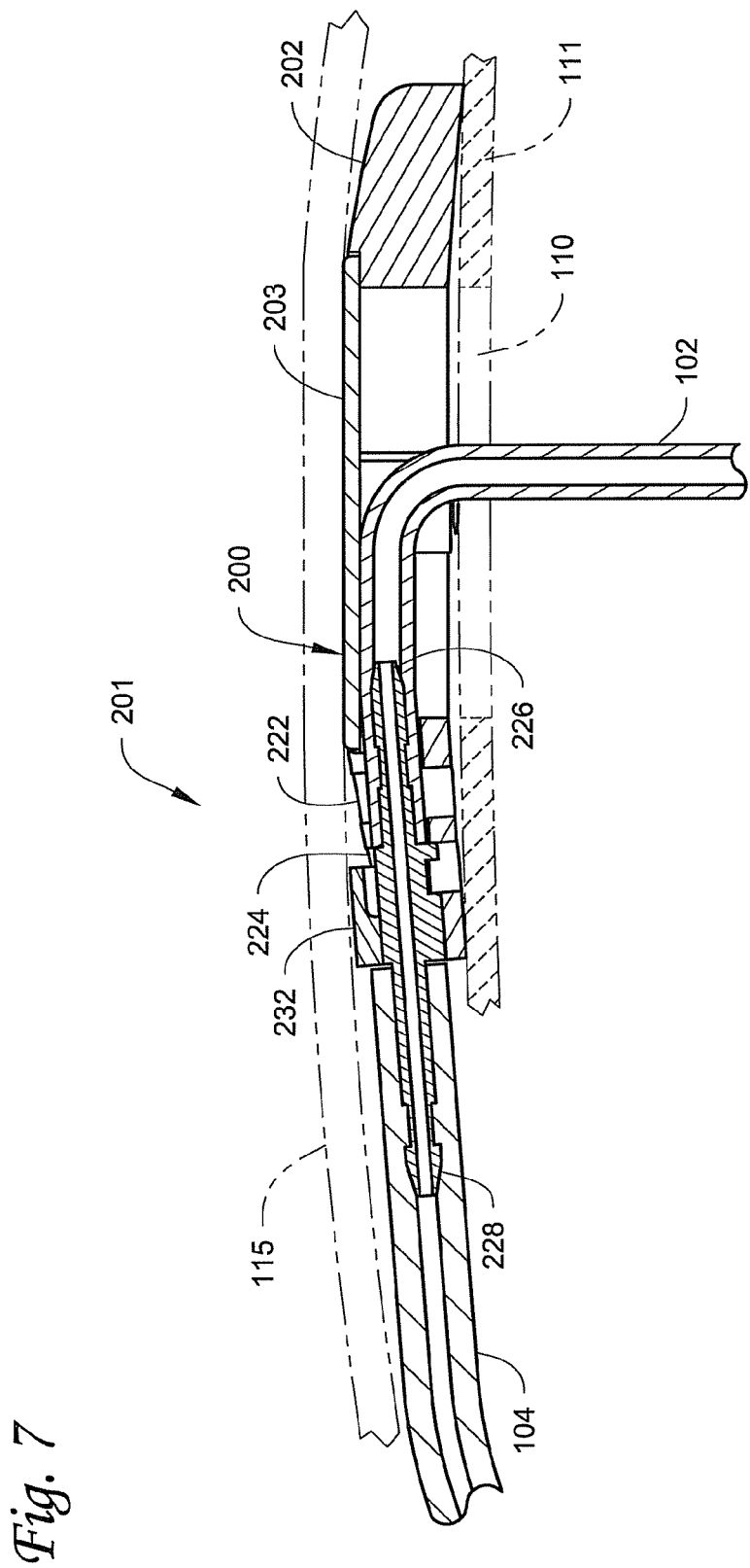
FIG. 7 is a partial cross sectional view of the anchor system of FIG. 1 after implantation.

FIG. 7 illustrates a section view of the assembled anchor system 201 after catheter interconnection and surgical implantation. As clearly shown in this view, the anchor base 202 is aligned over the burr hole 110 and secured to the skull 111 as described herein. With the base secured, the catheters 102 and 104 connected, and the cap 203 installed, the surgical incision in the skin 115 (made to access the skull 111) may be closed and the infusion system operated in accordance with the desired therapy delivery profile. Those of skill in the art will realize that the various components (e.g., catheters 102 and 104 and pin 204) of the system may be primed or otherwise purged of air prior to therapy initiation.

While illustrated in FIGS. 1-7 as providing an anti-rotate feature, the retaining member, e.g., clip 232, may, in another embodiment, be provided without such features. For example, the clip could be formed generally as a C-shaped member such that it includes the resilient legs 244 but not the body portion 246 as shown in FIG. 3. Such a clip embodiment could be provided where rotation of the catheters 102, 104 is restrained by another mechanism or is otherwise not of particular importance to the operation of the system.

FIGS. 8-15 illustrate a body portal (e.g., burr hole) anchor system 301 including an anchor (e.g., burr hole anchor 300) in accordance with yet another embodiment of the present invention. The anchor 300 is, as is evident from this description, similar in many respects to the anchor 200 and, in fact, may be substituted for the anchor 200 and vice-versa. For brevity, description of aspects of the anchor 300 that are common or similar to the anchor 200 (e.g., the catheters 102, 104, cap 203, aspects of the base 302, etc.) may not be repeated herein.

Although similar in many ways to the anchor 200 (e.g., the anchor 300 has a base 302 and a tubular connector 304 selectively attachable to the base), the system 301/anchor 300 may utilize a retaining member 332 that is captivated by the base 302. By captivating the retaining member 332, the anchor 300 may offer various benefits over non-captivated configurations. For example, the retaining member 332 may be automatically aligned relative to the base 302 prior to engagement with the connector 304, easing the engagement process. Moreover, the captivated retaining member 332 is not susceptible to being lost or misplaced before or during implantation. Still further, this embodiment directly keys to and aligns with the connector 304, eliminating the need to orient a keying feature on the retaining member before attachment.

Figure 8:
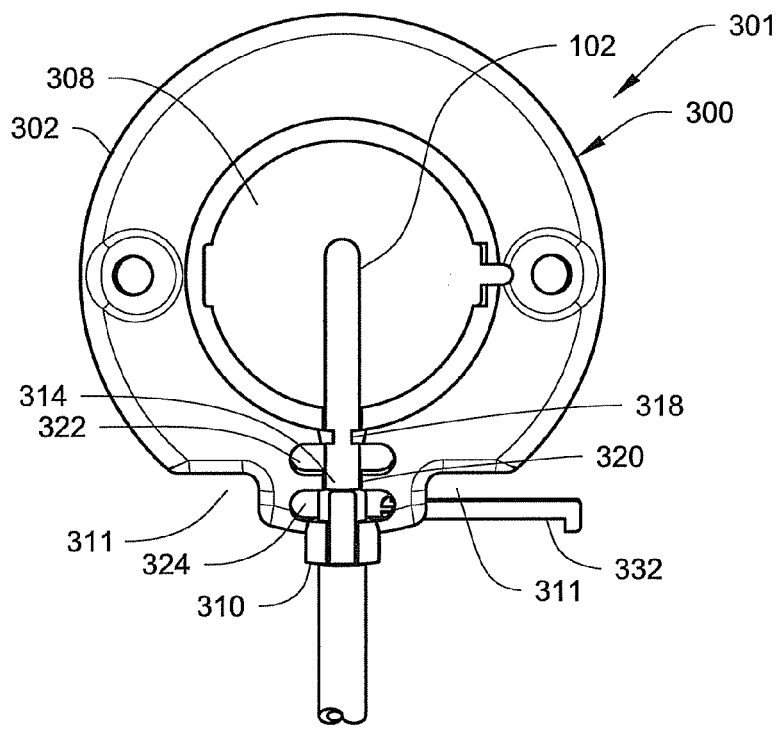
FIG. 8 is a top plan view of an anchor in accordance with another embodiment of the invention, wherein the anchor is shown with a therapy catheter located therein.

FIG. 8 is a top plan view of the annular base 302 of the anchor 300. As shown in this view, the base 302 may, like the base 202, include a catheter connection passage (which, in the illustrated embodiment, is a trough-like, recessed catheter connection channel 314 formed in a upper surface of the base) extending from its central opening 308 radially outward to and through its outer peripheral edge 310. Unlike the base 202, however, the outer peripheral edge 310 may have inwardly notched areas 311 on each side of the channel 314 to provide access to the retaining member 332 as further described below. While illustrated as having notched areas 311, alternative embodiments may maintain the round edge of the base, but permit the area in and around the channel 314 to extend radially outwardly beyond the round peripheral edge.

Figure 9:
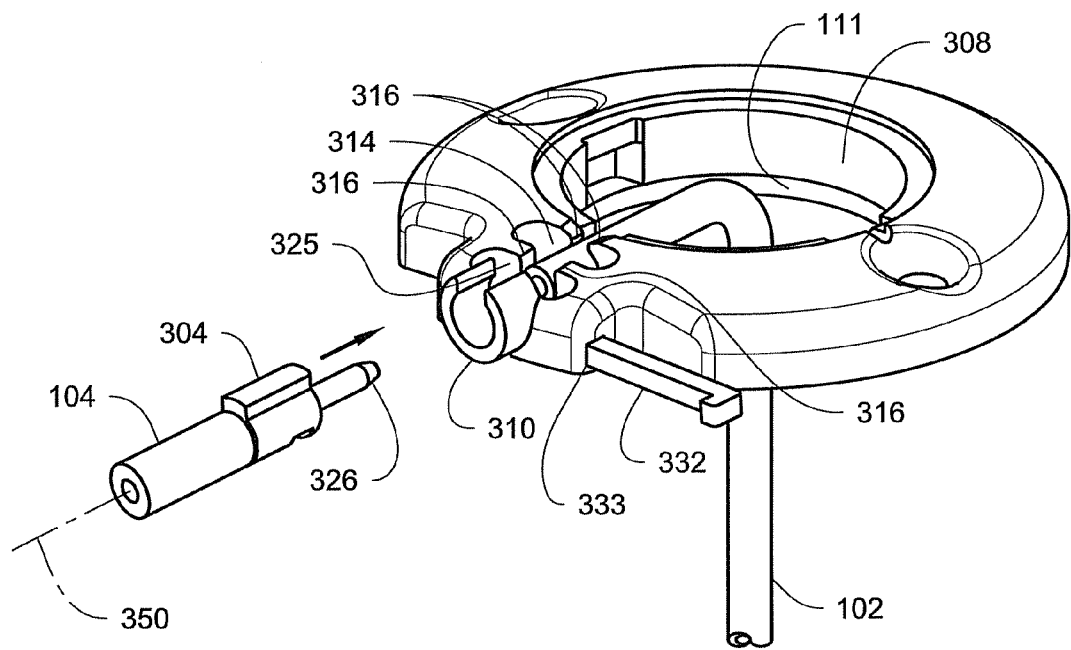
FIG. 9 is a perspective view of the anchor of FIG. 8 with the therapy catheter trimmed to length, but before attachment of a connector and delivery catheter.

As shown in FIGS. 8 and 9, the captive retaining member 332 may be formed as an elongate member or pin that is positionable (e.g., slides or translates within) an opening 333 formed in the base 302 between disengaged and engaged positions. The opening 333 may intersect the channel 314 such that the retaining member 332 may pass through (e.g., across) the channel as further described below. In one embodiment, the opening 333 and retaining member 332 extend completely through the channel in a direction transverse to a longitudinal axis 350 of the channel/connector 304 as shown. However, other orientations of the retaining member 332 are certainly possible without departing from the scope of the invention.

Once the therapy catheter 102 is positioned and the base 302 is secured to tissue (e.g., bone 111) in a manner as already described herein with respect to system 201, the terminal segment of the therapy catheter 102 may be positioned within the channel 314 where it is held in place by cinching surfaces 316 (e.g., at cinch points 318 and 320) that at least partially overhang and define the channel. The cinching surfaces are similar in form and function to the cinching surfaces 216 already described herein. The catheter 102 may then be cut to length in a manner substantially similar to that described with respect to anchor 200 (e.g., the catheter 102 may be held with forceps or the like via a first enlarged area 322 of the channel 314, while a surgical cutting tool is used to cut the catheter along a cut surface 325 formed in a second enlarged area 324). With the therapy catheter 102 cut to the appropriate length, as shown in FIG. 9, the connector 304 (either with or without the delivery catheter 104 attached) may be selectively inserted longitudinally into the channel 314 as indicated. The delivery catheter 102 may be held via the first enlarged area 322 while the connector 304 is introduced.

Figure 10:
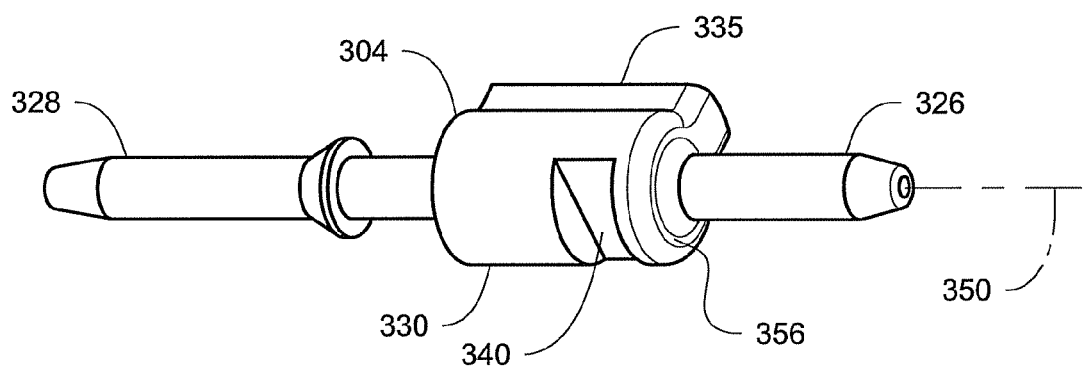
FIG. 10 is an enlarged view of the connector of FIG. 9.

FIG. 10 illustrates a bottom perspective view of the exemplary connector 304. Like the connector 204, the connector 304 may include a first end 326 defining a therapy tip for selective insertion into the channel 314, and an opposite or second end 328 defining a delivery tip. The connector 304 may further include an enlarged central portion 330 between the first and second ends. The first and second ends 326, 328 (e.g., the therapy tip and the delivery tip) may be configured for insertion into the lumens at first ends of, respectively, the therapy catheter 102 and the delivery catheter 104 when the connector 304 is fully inserted into the channel 314. Like the catheters of the system 201, the second end of the therapy catheter 102 may be located at the desired target site within the body, while the second end of the delivery catheter 104 may be connected to a therapy source (see, e.g., implantable infusion pump 106 illustrated in FIG. 1).

The enlarged central portion 330 of the connector 304 may include a cutout or slot. For instance, an outer surface of the central portion 330 may include a groove 340 that extends transverse to the longitudinal axis 350 of the connector. The groove 340 may be sized to receive at least a portion of the retaining member 332 when the latter is moved to an engaged position (and when the connector 304 is fully inserted into the channel 314 as further described below). The groove 340 is constructed to ensure that it does not intersect the lumen of the connector 304.

The central portion 330 may further define a longitudinal protrusion or ridge 335 running along a portion, e.g., a top edge, of the central portion. The ridge 335 may slide between anti-rotate keyway surfaces of the channel 314, thereby forming an anti-rotate key or the like to limit rotational movement of the connector 304 relative to the base 302. In addition to acting as an anti-rotate keyway, the ridge 335 also assists with aligning the groove 340 with the retaining member 332.

As the connector 304 is inserted into the channel 314, the therapy tip 326 may enter the lumen of the therapy catheter 102. During insertion, the therapy catheter 102 may be held in place with forceps or the like gripping the catheter via access through the first enlarged area 322 of the base. Alternatively, the channel may include other features that restrict longitudinal movement of the catheter 102. Eventually, an annular face 356 (see FIG. 10) of the connector 304 may contact the cut surface 325 of the base 302 (see FIG. 11) defined by a face of the second enlarged area 324. The cut surface 325 may limit further insertion of the connector into the channel. That is, the base 302 and connector 304 are configured such that, when this contact occurs, the connector is fully inserted into the channel 314 such that the groove 340 of the connector 304 (see FIG. 10) is aligned with the retaining member 332 (see FIG. 11).

Figure 11:
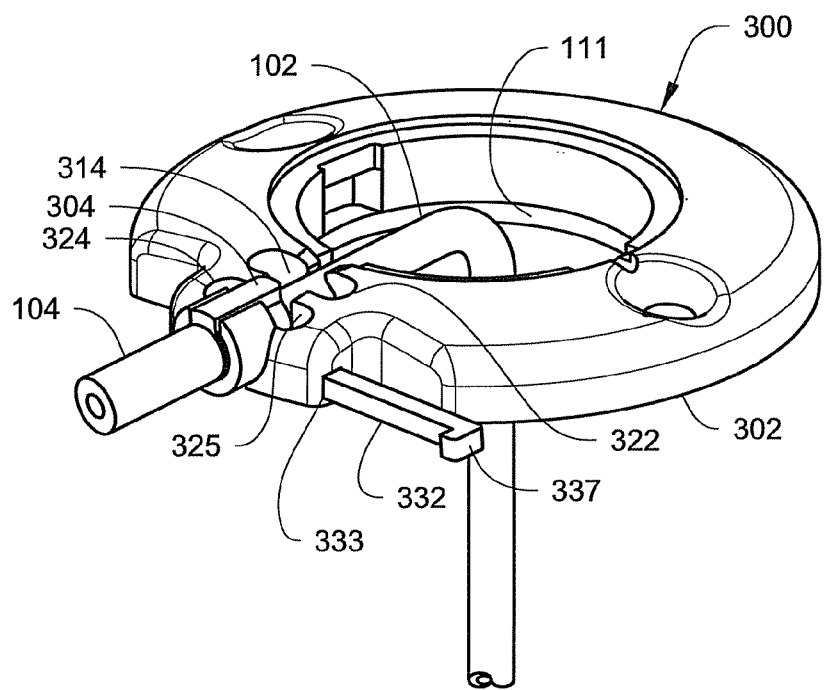
FIG. 11 is a perspective view of the anchor of FIG. 9 after attachment of the connector to the therapy catheter and with a retaining member shown in a disengaged position.
Figure 12:
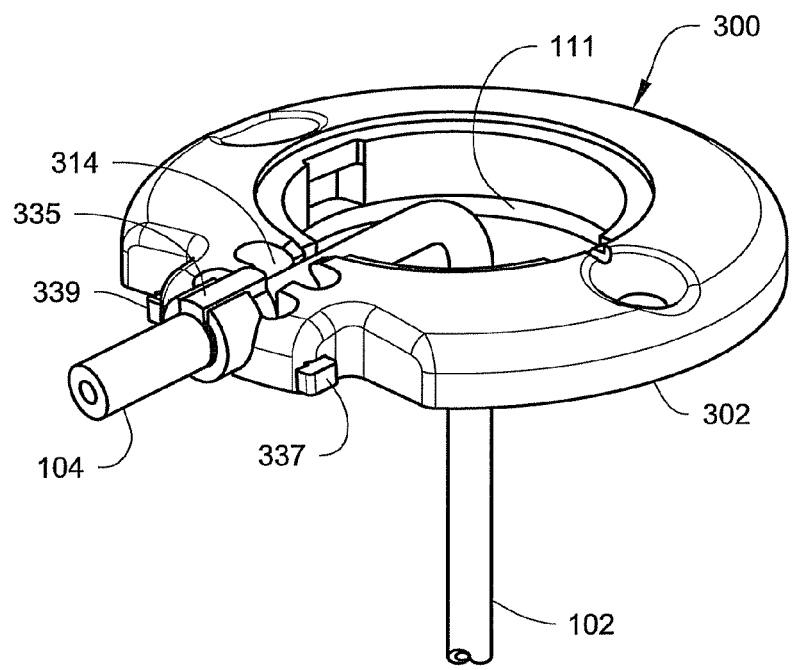
FIG. 12 is a perspective view of the anchor of FIG. 11 after movement of the retaining member to an engaged position.
Figure 13:
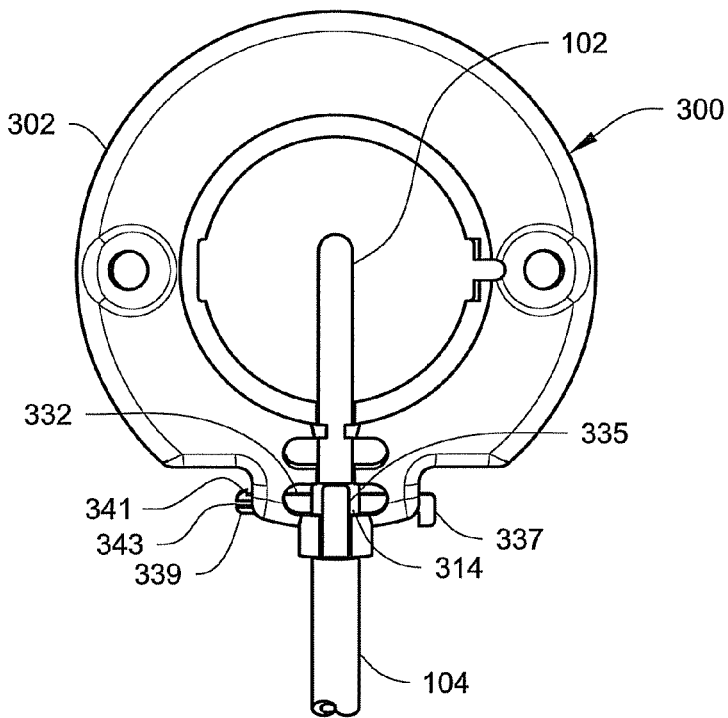
FIG. 13 is a top plan view of the anchor of FIG. 12.
Figure 14:
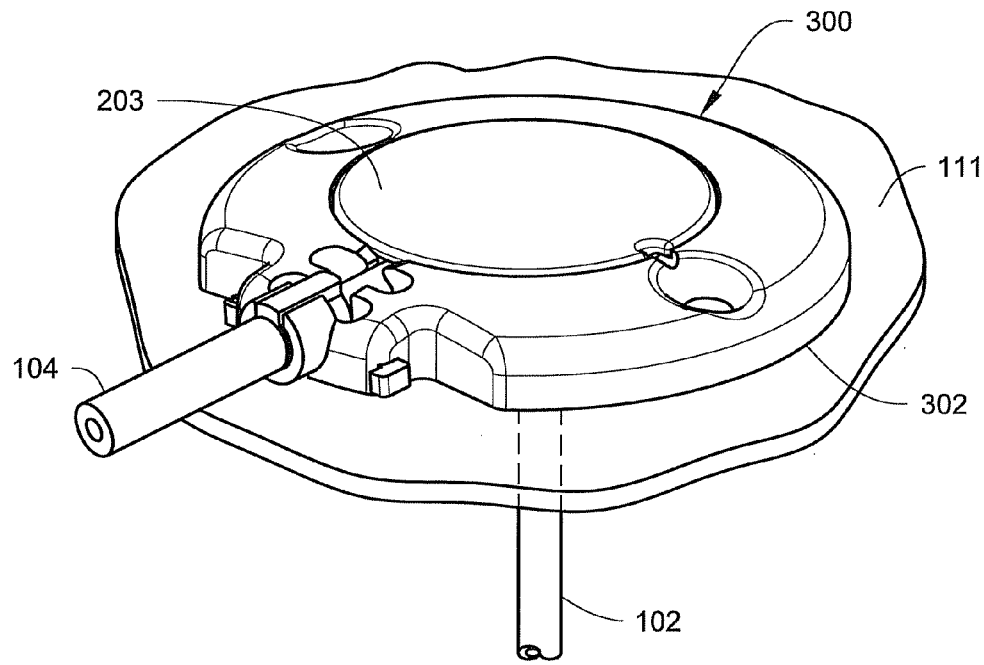
FIG. 14 is a perspective view of the anchor of FIG. 12 with a cap attached.

The retaining member 332 may be movable within the opening 333, when the connector is full inserted into the channel 314, between: a first or disengaged position as shown in FIG. 11; and a second or engaged position as shown in FIGS. 12-14. In the disengaged position, the retaining member 332 lies outside of the channel 314 (or protrudes only slightly into the channel). That is, in the disengaged position, the retaining member 332 is spaced-apart from the connector 304 (while the connector is being inserted (or is fully inserted) into the channel 314) such that the retaining member does not interfere with movement of the connector relative to the base (does not interfere with movement of the connector within the channel). The retaining member 332 and opening 333 may, in the illustrated embodiment, be rectangular (e.g., square) in cross section (with the groove 340 providing a complimentary shape). However, other shapes are possible within the scope of the invention.

However, once the connector 304 is fully inserted (e.g., once the annular face 356 of the connector 304 (see FIG. 10) contacts the cut surface 325 (see FIG. 11) of the channel 314), the clinician may manually actuate the retaining member 332 by applying a force to a button end 337. As this force is applied, the retaining member 332 may move from the disengaged position (see FIG. 11) to the engaged position (see FIG. 12). This causes the retaining member 332 to extend or pass through the channel 314 and into the aligned groove 340 (see FIG. 10) formed in the connector 304. When fully depressed as shown in FIGS. 12 and 13, a distal end 339 of the retaining member 332 may protrude beyond an opposite side of the base 302. Accordingly, when moved to the engaged position, the retaining member 332 engages or contacts the connector 304 (as well as the base 302) and immobilizes the connector relative to the base (e.g., the retaining member 332 effectively attaches the connector to the base).

When the connector 304 is fully inserted into the base 302 as shown in FIGS. 12 and 13, the ridge 335 of the connector may be captivated against rotation by surfaces of the base 302 that form the channel 314. As a result, the connector 304 (and thus the catheters 102 and 104) is generally restricted from rotation relative to the base 302.

As further shown in FIG. 13, the distal end 339 of the retaining member 332 may include a tab 341 or the like. The tab 341 may protrude sufficiently to prevent the retaining member 332 from moving from its engaged position back towards the disengaged position, thus providing positive locking or capture of the retaining member when in the engaged position. In the illustrated embodiment, the tab 341 may have a ramped or rounded nose to permit it to push easily through the opening of the base 302 as the retaining member is moved towards the engaged position.

Moreover, the distal end 339 of the retaining member 332 may include a slot 343 as shown in FIG. 13. The slot may permit the tab 341 of the retaining member 332 to deflect. As a result, the tab 341 may travel within the opening 333 formed through the base 302 when the retaining member is moved towards the engaged position. However, the tab may resiliently return to its undeflected position shown in FIG. 13 upon the retaining member reaching the engaged position. The tab 341 and slot 343 may also prevent the retaining member from sliding out of the base 302 when the retaining member is in the disengaged position (e.g., as shown in FIG. 8, the tab may keep the distal end 339 from sliding out (beyond the disengaged position) by captivating the tab 341 within the channel 314).

Once the retaining member 332 is engaged with the connector 304 as described herein, the connector may be immobilized relative to the base 302. As a result, extraneous forces acting on the therapy catheter 104 may be isolated by the connector such that they transfer little or no displacement loads to the therapy catheter 102.

FIG. 14 illustrates the anchor 300 after attachment of the exemplary cap 203, which may attach to the base 302 in a manner substantially similar to the base 202 described above.

Figure 15:
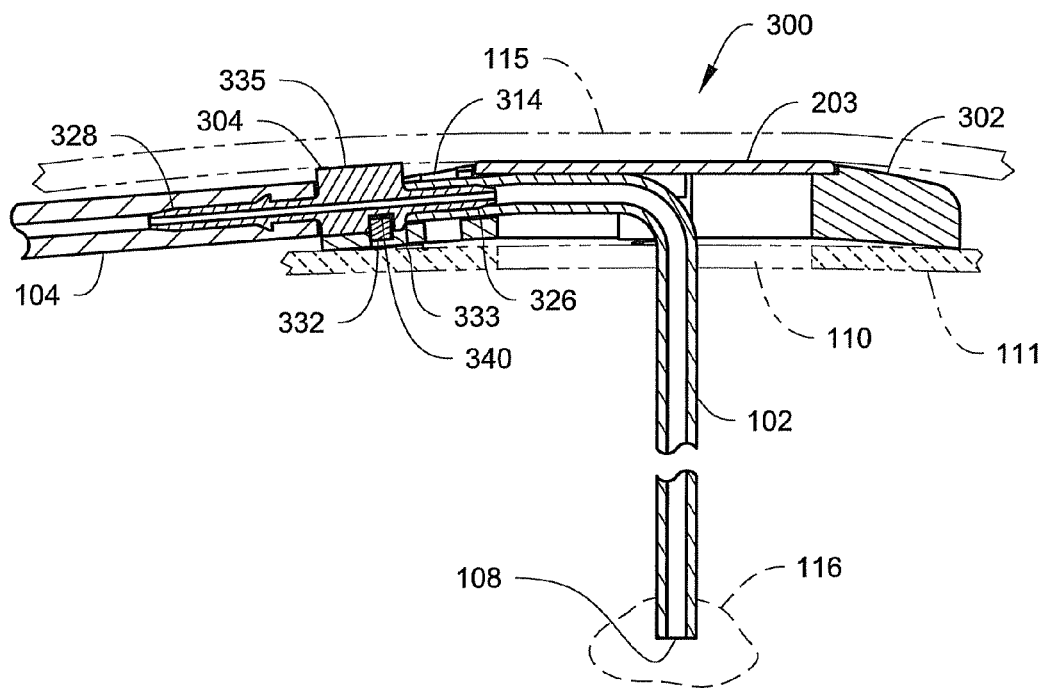
FIG. 15 is a section view taken through the anchor of FIG. 14 illustrating the interaction of the retaining member with the connector.

FIG. 15, illustrates a section view of the anchor of FIG. 14. In this view, the base 302, catheters 102, 104, connector 304, and retaining member 332 are visible with the retaining member shown in the engaged position and the connector shown fully inserted into the channel 314. As shown in this view, the connector 304 may fluidly couple to both the terminal segment of the therapy catheter 102 and the delivery catheter 104, permitting fluid conveyance from the delivery catheter to the therapy catheter.

Once again, while illustrated herein in the context of specific exemplary embodiments, variations are certainly possible without departing from the scope of the invention. For example, while illustrated with only a single delivery catheter 104 and therapy catheter 102, other embodiments may utilize additional delivery and/or therapy catheters where beneficial to the specific application.

Anchors and systems in accordance with embodiments of the present invention may provide various benefits including, for example, isolating the therapy catheter from forces that may otherwise be transmitted thereto by the delivery catheter. As a result, the delivering tip of the therapy catheter may be less likely to be displaced during the implantation period. Further, for example, anchors in accordance with embodiments of the present invention permit attachment of the catheter connector to the anchor base after the base has been attached to tissue and after the therapy catheter has been positioned.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A body portal anchor system comprising:
   a base operable to secure to tissue surrounding a body portal;
   a connector selectively attachable to the base, wherein the connector, when attached to the base, is operable to fluidly connect with a terminal segment of a therapy catheter associated with the base; and
   a retaining member movable, relative to the base, between: a disengaged position, wherein the retaining member is spaced-apart from the connector so that the connector may move relative to the base; and an engaged position, wherein the retaining member engages the connector and attaches the connector to the base;
   wherein the base defines a catheter connection passage configured to receive both the terminal segment of the therapy catheter and a first end of the connector, wherein the passage forms a trough-like channel in an upper surface of the base, the channel being partially covered by overhanging cinching surfaces, and further wherein the first end of the connector is adapted for insertion into both the passage and a lumen of the therapy catheter.

2. The system of claim 1, wherein the retaining member comprises a pin translatable within an opening formed in the base, the pin configured to engage a slot formed in the connector when the connector is inserted into the passage and the retaining member is in the engaged position.

3. The system of claim 1, wherein the connector further comprises a second end adapted for insertion into a lumen of a delivery catheter.

4. The system of claim 1, wherein either the retaining member or the connector comprises an anti-rotate key configured to limit rotational movement of the connector relative to the base when the connector is inserted into the passage and the retaining member is in the engaged position.

5. The system of claim 1, wherein the passage is configured to limit movement of the connector in a direction transverse to a longitudinal axis of the passage.

6. The system of claim 1, wherein the base defines a central opening and wherein the passage extends from the central opening outwardly through a peripheral edge of the base.

7. The system of claim 6, further comprising a cap, the cap attachable to the base to cover the central opening.

8. A burr hole anchor system comprising:
   an annular base adapted to secure to bone surrounding a burr hole, wherein the base comprises a peripheral edge and further defines a central opening, wherein a catheter connection passage extends from the central opening outwardly through the peripheral edge;
   a connector selectively attachable to the base, wherein the connector, when attached to the base, is adapted to fluidly connect with a terminal segment of a therapy catheter associated with the base; and
   a retaining member movable, relative to the base, between: a disengaged position, wherein the retaining member is spaced-apart from the connector so that the connector may move relative to the base; and an engaged position, wherein the retaining member engages the connector and attaches the connector to the base;
   wherein the passage is configured to receive both the terminal segment of the therapy catheter and a first end of the connector, wherein the passage forms a trough-like channel in an upper surface of the base, the channel partially covered by overhanging cinching surfaces, and further wherein the first end of the connector is adapted for insertion into a lumen of the therapy catheter.

9. The system of claim 8, wherein the retaining member comprises a pin translatable within an opening formed in the base, the pin configured to engage a slot formed in the connector when the connector is inserted into the passage and the retaining member is in the engaged position.

10. The system of claim 8, wherein the connector further comprises a second end adapted for insertion into a lumen of a delivery catheter.

11. The system of claim 8, wherein either the retaining member or the connector comprises an anti-rotate key configured to limit rotational movement of the connector relative to the base when the connector is inserted into the passage and the retaining member is in the engaged position.

12. A body portal anchor system comprising:
   a base operable to secure to tissue surrounding a body portal;
   a connector selectively attachable to the base, wherein the connector, when attached to the base, is operable to fluidly connect with a terminal segment of a therapy catheter associated with the base; and
   a retaining member movable, relative to the base, between: a disengaged position, wherein the retaining member is spaced-apart from the connector so that the connector may move relative to the base; and an engaged position, wherein the retaining member engages the connector and attaches the connector to the base, and further wherein the retaining member moves along a direction transverse to a longitudinal axis of the connector as the retaining member moves between the disengaged and engaged positions;

wherein the base defines a catheter connection passage configured to receive both the terminal segment of the therapy catheter and a first end of the connector, and further wherein the first end of the connector is adapted for insertion into both the passage and a lumen of the therapy catheter.

13. The system of claim 12, wherein the passage forms a trough-like channel in an upper surface of the base, the channel partially covered by overhanging cinching surfaces.

14. The system of claim 12, wherein the retaining member comprises a pin translatable within an opening formed in the base, the pin configured to engage a slot formed in the connector when the connector is inserted into the passage and the retaining member is in the engaged position.

15. The system of claim 12, wherein the connector further comprises a second end adapted for insertion into a lumen of a delivery catheter.

16. The system of claim 12, wherein either the retaining member or the connector comprises an anti-rotate key configured to limit rotational movement of the connector relative to the base when the connector is inserted into the passage and the retaining member is in the engaged position.

17. The system of claim 12, wherein the passage is configured to limit movement of the connector in a direction transverse to a longitudinal axis of the passage.

18. The system of claim 12, wherein the base defines a central opening and wherein the passage extends from the central opening outwardly through a peripheral edge of the base.

19. The system of claim 18, further comprising a cap, the cap attachable to the base to cover the central opening.

20. A body portal anchor system comprising:
a base operable to secure to tissue surrounding a body portal;
a connector selectively attachable to the base, wherein the connector, when attached to the base, is operable to fluidly connect with a terminal segment of a therapy catheter associated with the base; and
a retaining member movable, relative to the base, between: a disengaged position, wherein the retaining member is spaced-apart from the connector so that the connector may move relative to the base; and an engaged position, wherein the retaining member engages the connector and attaches the connector to the base, and further wherein the retaining member comprises opposing resilient legs configured to be received partially within a circumferential groove formed in an outer surface of the connector;

wherein the base defines a catheter connection passage configured to receive both the terminal segment of the therapy catheter and a first end of the connector, and further wherein the first end of the connector is adapted for insertion into both the passage and a lumen of the therapy catheter.

21. The system of claim 20, wherein the passage forms a trough-like channel in an upper surface of the base, the channel partially covered by overhanging cinching surfaces.

22. The system of claim 20, wherein the retaining member comprises a pin translatable within an opening formed in the base, the pin configured to engage a slot formed in the connector when the connector is inserted into the passage and the retaining member is in the engaged position.

23. The system of claim 20, wherein the connector further comprises a second end adapted for insertion into a lumen of a delivery catheter.

24. The system of claim 20, wherein either the retaining member or the connector comprises an anti-rotate key configured to limit rotational movement of the connector relative to the base when the connector is inserted into the passage and the retaining member is in the engaged position.

25. The system of claim 20, wherein the passage is configured to limit movement of the connector in a direction transverse to a longitudinal axis of the passage.

26. The system of claim 20, wherein the base defines a central opening and wherein the passage extends from the central opening outwardly through a peripheral edge of the base.

27. The system of claim 26, further comprising a cap, the cap attachable to the base to cover the central opening.

* * * * *